US010309910B2

(12) United States Patent
Sharma et al.

(10) Patent No.: US 10,309,910 B2
(45) Date of Patent: Jun. 4, 2019

(54) SYSTEM AND METHOD TO MEASURE SALINITY OF MULTI-PHASE FLUIDS

(71) Applicant: General Electric Company, Schenectady, NY (US)

(72) Inventors: Prafull Sharma, Karnataka (IN); Aparna Chakrapani Sheila-Vadde, Karnataka (IN)

(73) Assignee: General Electric Company, Schenectady, NY (US)

( * ) Notice: Subject to any disclaimer, the term of this patent is extended or adjusted under 35 U.S.C. 154(b) by 35 days.

(21) Appl. No.: 14/936,850

(22) Filed: Nov. 10, 2015

(65) Prior Publication Data
US 2016/0131601 A1    May 12, 2016

(30) Foreign Application Priority Data
Nov. 10, 2014    (IN) .......................... 5644/CHE/2014

(51) Int. Cl.
*G01R 22/00*    (2006.01)
*G01N 33/00*    (2006.01)
(Continued)

(52) U.S. Cl.
CPC .......... *G01N 22/00* (2013.01); *G01N 33/0004* (2013.01); *G01N 33/2823* (2013.01)

(58) Field of Classification Search
CPC .............. G01N 22/00; G01N 33/0004; G01N 33/2823; G01N 33/18; G01N 33/28;
(Continued)

(56) References Cited

U.S. PATENT DOCUMENTS

| 4,902,961 A | 2/1990 | De et al. |
| 5,101,163 A * | 3/1992 | Agar ...................... G01N 22/00 |
| | | 324/639 |

(Continued)

OTHER PUBLICATIONS

Ebbe et al., "Measuring the salt content of the water, the composition, and flow, of a wet gas stream using microwaves, differential pressure, and PVT calculations", Instrumentation and Measurement Technology Conference, 2004. IMTC 04. Proceedings of the 21st IEEE, vol. 3, pp. 2288-2291, May 18-20, 2004.

(Continued)

*Primary Examiner* — Tung X Nguyen
*Assistant Examiner* — Lee E Rodak
(74) *Attorney, Agent, or Firm* — Mintz Levin Cohn Ferris Glovsky and Popeo, P.C.

(57) ABSTRACT

A method of determining salinity of multi-phase fluids in a conduit includes exciting a sensing device to cause emission of electromagnetic waves of one or more frequencies into the multi-phase fluid. The method includes receiving transmitted or reflected electromagnetic waves from the multi-phase fluid. Furthermore, the method includes determining an intermediate parameter from the received electromagnetic waves. The method also includes obtaining estimated values of a plurality of parameters from the intermediate parameter. The estimated values comprise at least one of an estimated value of conductance, an estimated value of susceptance, an estimated value of differential conductance, an estimated value of differential susceptance, an estimated value of a real part of complex permittivity, and an estimated value of an imaginary part of complex permittivity. Salinity of the fluid is determined based, at least in part, on the estimated values of the plurality of parameters.

13 Claims, 3 Drawing Sheets

(51) Int. Cl.
*G01N 33/28* (2006.01)
*G01N 27/06* (2006.01)
*G01N 22/00* (2006.01)

(58) Field of Classification Search
CPC ....... G01N 33/2847; G01F 1/66; G01F 1/662; G01F 1/712; G01F 1/74
USPC .......... 324/94, 204, 324, 453, 522, 637, 638, 324/642, 643, 646, 664, 693, 694, 713; 73/1.02, 61.44, 152.18
See application file for complete search history.

(56) References Cited

U.S. PATENT DOCUMENTS

| | | | |
|---|---|---|---|
| 5,107,219 A | 4/1992 | Marrelli et al. | |
| 5,233,306 A * | 8/1993 | Misra | G01R 27/2623 324/601 |
| 5,243,290 A | 9/1993 | Safinya et al. | |
| 5,259,239 A | 11/1993 | Gaisford | |
| 5,485,743 A | 1/1996 | Taherian et al. | |
| 5,576,974 A | 11/1996 | Marrelli et al. | |
| 5,596,150 A * | 1/1997 | Arndt | G01F 1/64 73/861.12 |
| 5,675,259 A | 10/1997 | Arndt et al. | |
| 6,182,504 B1 | 2/2001 | Gaisford | |
| 6,466,035 B1 | 10/2002 | Nyfors et al. | |
| 6,826,964 B2 | 12/2004 | Nyfors | |
| 6,831,470 B2 | 12/2004 | Xie et al. | |
| 6,915,707 B2 | 7/2005 | Nyfors et al. | |
| 7,133,786 B1 | 11/2006 | Dykesteen et al. | |
| 7,469,188 B2 | 12/2008 | Wee | |
| 7,481,118 B2 | 1/2009 | Nyfors | |
| 7,624,652 B2 | 12/2009 | Wee et al. | |
| 7,631,543 B2 | 12/2009 | Wee | |
| 7,712,381 B2 | 5/2010 | Allenberg et al. | |
| 7,770,469 B2 | 8/2010 | Nyfors et al. | |
| 8,536,883 B2 | 9/2013 | Xie et al. | |
| 2003/0011386 A1* | 1/2003 | Xie | G01N 33/2823 324/694 |
| 2006/0145709 A1* | 7/2006 | Bentolila | G01N 22/00 324/717 |
| 2006/0265150 A1* | 11/2006 | Hu | G01N 33/2823 702/50 |
| 2008/0303534 A1 | 12/2008 | Wee | |
| 2008/0319685 A1 | 12/2008 | Xie et al. | |
| 2009/0088985 A1 | 4/2009 | Wee | |
| 2009/0267617 A1* | 10/2009 | Seyfi | G01N 27/023 324/655 |
| 2010/0064820 A1* | 3/2010 | David | G01N 33/2823 73/861.04 |
| 2010/0145634 A1* | 6/2010 | Pinguet | G01F 1/46 702/45 |
| 2010/0262371 A1* | 10/2010 | Oraby | G01V 5/104 702/8 |
| 2011/0098938 A1 | 4/2011 | Huang et al. | |
| 2011/0196625 A1 | 8/2011 | Sheila-Vadde et al. | |
| 2011/0267074 A1* | 11/2011 | Xie | G01N 22/00 324/629 |
| 2013/0110411 A1* | 5/2013 | Black | G01N 27/02 702/23 |
| 2013/0327154 A1* | 12/2013 | Xie | G01N 33/28 73/861.04 |
| 2015/0226683 A1* | 8/2015 | Feldman | A01J 5/0133 324/640 |

OTHER PUBLICATIONS

Tjugum et al., "A compact low energy multibeam gamma-ray densitometer for pipe-flow measurements", Nuclear Instruments and Methods in Physics Research Section B: Beam Interactions with Materials and Atoms, ScienceDirect, vol. 197, Issues 3-4, pp. 301-309, Dec. 2002.

Stogrym, "Equations for calculating the dielectric constant of saline water", IEEE Transactions on Microwave Theory and Techniques, vol. No. 19, Issue No. 8, pp. 733-736, Aug. 1971.

* cited by examiner

SYSTEM AND METHOD TO MEASURE SALINITY OF MULTI-PHASE FLUIDS

BACKGROUND

Embodiments of the present invention relates generally to the field of multi-phase flow metering and, more particularly, to a method and system for determining salinity in multi-phase fluids.

A multi-phase fluid refers to a composition that includes at least two phases of material. For example, multi-phase fluids may include some combination of oil, water, and gas. In process industries, oil and gas industries and other such areas, it is often necessary to accurately measure fractions and flow rate of phases of the multi-phase fluid flowing inside a pipeline. With smaller and deeper oil/gas wells with higher water content becoming more common around the globe, there is an enhanced need for multi-phase flow measurement techniques.

Commercially available sensors for measuring fractions in fluids in the petroleum industry are based on a variety of principles (either a single technique or a combination of several techniques). For example, impedance sensors, capacitive and/or inductive sensors, dual-energy gamma sensors, venturi meters, and microwave sensors (attenuation/phase/resonance) have all been used. Currently, there are numerous microwave-based flow metering sensors available offering varying degrees of sensitivity, complexity and costs.

Accuracy of current fraction measurement systems may be affected by the presence of saline content in the water phase of the multi-phase fluid. Presence of saline content leads to changes in the permittivity of the multi-phase fluid. If salinity is not determined accurately, changes in permittivity can be incorrectly attributed to changes in water fraction for instance. The measurements therefore need to be compensated for salinity for accurate fraction measurements.

Further, salinity determination helps users of the measurement facility to take control actions. Control actions pertaining to descaling of conduits are particularly dependent on measuring salinity in the multi-phase fluids flowing through the conduits. Metallic conduits may experience corrosion due to deposition of saline material on the inner surface of the conduits that is exposed to the multi-phase fluid. Hence, measuring saline content in the fluid flowing through the conduit is important.

Current salinity measurement systems include systems that are dependent on using phase differences observed in electromagnetic waves received at different sensing antennas. However, phase difference methodologies have been observed to provide accurate results in limited cases for multi-phase fluids with low dielectric losses (for example: oil-continuous fluids and wet gas streams).

Other existing systems and methods include determining reflection coefficients of reflected electromagnetic waves received from the multi-phase fluid, determining conductivity from the reflection coefficients and estimating salinity based on a conductive loss term in the permittivity associated with the fluid. Permittivity of water ($\varepsilon_r w$) can be expressed as follows:

$$\varepsilon_r(w) = \varepsilon'_r - j\left(\varepsilon''_r + \frac{\sigma}{\omega\varepsilon_0}\right)$$

where, $\varepsilon'_r$ corresponds to a real part of permittivity, $\varepsilon''_r$ corresponds to the dielectric loss term, $$\frac{\sigma}{\omega\varepsilon_0}$$

represents the conductive loss term, where $\sigma$ is the conductivity, $\omega$ is the angular frequency and $\varepsilon_0$ is the permittivity of free space.

As can be seen from the equation the conductive loss term is inversely proportional to frequency and hence decreases with an increase in frequency and becomes an insignificant value at higher frequencies. On the other hand, the dielectric loss term increases with frequency until resonance is achieved and then decreases with frequency. The resonance frequency, depending on the composition of multi-phase fluids, may be in the range of tens of GHz. When the operating range are in the range where the dielectric loss term is significant, current methods that depend on determining only the conductive loss term and ignore the dielectric loss term may produce erroneous results.

Accordingly, there is an ongoing need for multi-phase flow metering systems and methods that determine saline content in multi-phase fluids across all frequency ranges and for multi-phase fluids that contain substantial amounts of lossy medium.

BRIEF DESCRIPTION

In accordance with one embodiment of the present invention, a method of determining salinity of a multi-phase fluid in a conduit is provided. The method includes exciting a sensing device to cause the sensing device to emit electromagnetic waves of one or more frequencies into a multi-phase fluid. The method also includes receiving at least one of transmitted or reflected electromagnetic waves from the multi-phase fluid. The method further includes determining an intermediate parameter from the transmitted or reflected electromagnetic waves. Furthermore, the method includes obtaining estimated values of a plurality of parameters. The estimated values include at least one of an estimated value of conductance, an estimated value of susceptance, an estimated value of differential conductance, an estimated value of differential susceptance, an estimated value of a real part of complex permittivity, and an estimated value of an imaginary part of complex permittivity. The method includes determining the salinity of the multi-phase fluid based, at least in part, on the estimated values of the plurality of parameters.

In accordance with another embodiment of the present invention, a system for determining salinity of a multi-phase fluid flowing in a conduit is provided. The system includes a sensing device placed on or about the conduit and configured to emit electromagnetic waves of one or more frequencies. Further, the system also includes a controller that is configured to excite the sensing device to emit electromagnetic waves of the one or more frequencies towards the multi-phase fluid. The controller is further configured to acquire transmitted or reflected electromagnetic waves corresponding to the one or more frequencies from the multi-phase fluid. Further, the controller is configured to obtain estimated values of a plurality of parameters from the transmitted or reflected electromagnetic waves. The estimated values of the plurality of parameters include at least one of an estimated value of conductance, an estimated value of susceptance, an estimated value of differential conductance, an estimated value of differential susceptance, an estimated value of a real part of complex permittivity, and an estimated value of an imaginary part of complex permittivity. Furthermore, the controller is configured to determine the salinity of the multi-phase fluid based, at least in part, on at least one of the plurality of parameters.

DRAWINGS

The features and advantages of the present invention will become apparent from the following detailed description of the invention when read with the accompanying drawings in which.

DETAILED DESCRIPTION

Figure 1:
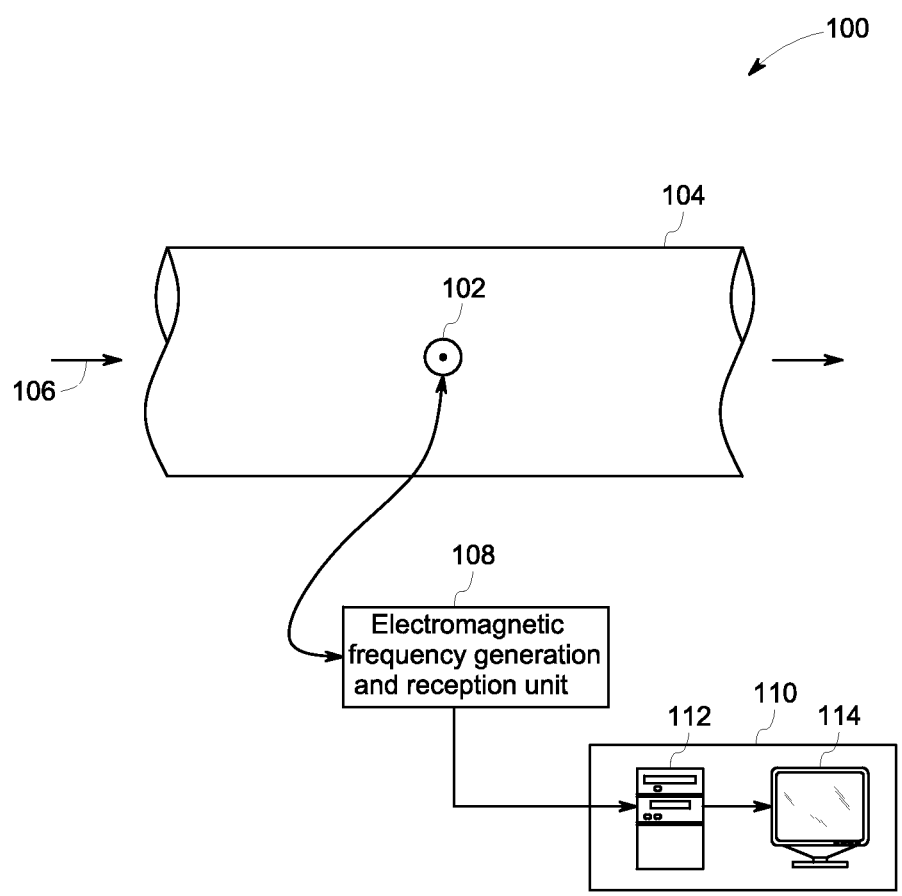
FIG. 1 is a diagrammatical representation of a multi-phase flow measurement system using at least one sensing device.

While embodiments of the present invention have been shown and described herein, such embodiments are provided by way of example only. Numerous variations, changes and substitutions will occur to those of skill in the art without departing from the invention herein. Accordingly, it is intended that the invention be limited only by the spirit and scope of the appended claims.

As will be discussed in detail below, embodiments of the invention include a method and system to detect saline content in multi-phase fluids. The term 'multi-phase,' as used herein, is used to refer to a composition that includes at least two phases of materials. Multi-phase fluids may include some combination of oil, water, and gas. For example, a particular sample of multi-phase fluid flowing through a conduit may include gas and water. In one example, the water may be saline water. In another example, the fluid may include gas and oil. The term 'conduit,' as used herein, refers to any structure that permits a flow of the multi-phase fluid. Further, the term conduit is not limited to elements that have a substantially circular cross-section, are substantially closed, or are longitudinal elements.

In accordance with embodiments of the invention, the determination of saline content includes emitting one or more frequencies in the microwave frequency range in the multi-phase fluid flowing through the conduit and measuring the reflected and/or transmitted signals. The term 'microwave frequency range' is used to refer to electromagnetic frequencies between hundreds of MHz to several hundreds of GHz. The electromagnetic waves are emitted by an antenna that is a part of a sensing device. The term 'antenna,' as used herein, may be used to refer to a transmitting and/or receiving element that is capable of operating at microwave frequencies. The antenna may be an open-ended coaxial probe that is configured to emit electromagnetic waves and receive transmitted or reflected electromagnetic waves from the multi-phase fluid. In another embodiment, the antenna may also include one or more metal portions over a ground plane, where the one or more metal portions and the ground plane are separated by one or more substrates.

In one embodiment, the antennas in the sensing devices emit electromagnetic waves over a range of frequencies and the transmitted or reflected electromagnetic waves are measured over that frequency range. The transmitted or reflected electromagnetic waves are utilized to determine a plurality of intermediate parameters. These intermediate parameters include a reflection coefficient associated with the reflected electromagnetic waves or transmission coefficient associated with the transmitted electromagnetic waves. The intermediate parameters may be utilized to determine a permittivity (dielectric constant) of the multi-phase fluid inside the conduit. The dielectric constant is a complex property including a real part and an imaginary part. Salinity in the multi-phase fluid causes changes in the dielectric properties of the fluid. These changes in the dielectric properties are utilized to measure the volume of salinity in the multi-phase fluid. Salinity changes also affect different parameters such as conductance, susceptance, and admittance. These parameters are determined from the reflection or transmission coefficients and utilized to measure the saline content in the multi-phase fluid.

FIG. 1 depicts a diagrammatical representation of a multi-phase flow measurement system 100 including one or more sensing devices 102. Each sensing device 102 includes an antenna that is configured to emit electromagnetic waves in the microwave frequency range. The sensing devices 102 may be disposed on a conduit 104. In particular, the sensing devices 102 may be placed in close proximity to a multi-phase fluid 106 flowing through the conduit 104. The multi-phase fluid may include fractions of different phases such as oil, water, and gas. In certain embodiments, the multi-phase fluid may include one or more lossy phases. Examples of lossy phase include, but are not limited to, water and water that may have dissolved in it, different components such as salts. Salts such as Sodium Chloride, Magnesium Chloride, and the like may be present in the multi-phase fluid. Based on the fluid that has a major contribution in the multi-phase fluid, the multi-phase fluid flow state may be categorized as an oil-continuous flow state or a water-continuous flow state. In the oil-continuous flow state, the multi-phase fluid 106 has water dispersed in oil and oil constitutes the continuous medium. Whereas, in the water-continuous state, oil is dispersed in water.

The sensing devices 102 may be excited to emit electromagnetic waves over a range of frequencies. The range of frequencies may include a range of microwave frequencies. By way of example, the range of frequencies may range from about 300 MHz to about 300 GHz.

The system 100 may also include an electromagnetic frequency generation and reception (EMFGR) unit 108. The EMFGR unit 108 may be configured to cause the one or more sensing devices 102 to emit electromagnetic waves of the desired range of frequencies. The EMFGR unit 108 may include an electronic device. In one example, the electronic device may include a vector network analyzer (VNA). Furthermore, the EMFGR unit 108 may be operatively coupled to a controller 110. The controller 110 may be programmable logic controller (PLC) or programmable automation controller (PAC). The controller 110 may include a graphical user interface 114 and a processing unit 112 that may be configured to control the operations of the EMFGR unit 108. In one example, the graphical user interface 114 may include a display unit. In one example, the graphical user interface 114 may be configured to display the data processed by the processing unit 112.

The antennas from the sensing devices 102 and the multi-phase fluid 106 in the conduit 104 may be represented as an electrical network that has a plurality of ports. The electrical network may be represented as a two-port network and may be analyzed using S-parameters. The ports are points at which electrical signals either enter and/or exit the electrical network. The S-parameter may be represented by a unit-less complex number that represents a magnitude and an angle, such as amplitude and a phase angle of the transmitted or reflected electromagnetic waves. A two-port electrical network may be represented by the S-parameters S11, S12, S21, and S22. S11 parameters represent amplitude and phase angle, associated with reflected electromagnetic wave at each frequency received at a first port in response to electromagnetic waves incident at the first port. Similarly, S12 parameters represent amplitude and phase angle, associated with transmitted electromagnetic wave received at the first port in response to electromagnetic waves incident at the second port. Moreover, S21 parameters are associated with electromagnetic waves received at the second port in response to incident electromagnetic waves emitted by the first port, while S22 represents parameters associated with electromagnetic waves received at the second port in response to electromagnetic waves incident at the second port.

In the system 100, the two ports of the electrical network may correspond to the ports of the sensing devices 102 that are coupled to the EMFGR unit 108. The sensing devices 102 may be excited to emit electromagnetic waves of the range of frequencies via use of an incident signal generated by the EMFGR unit 108. The incident signal is representative of a signal which is provided as an input to a port associated with one of the sensing devices 102 by the EMFGR unit 108. The electromagnetic waves emitted by the one of the sensing devices 102 may either be transmitted to an opposite end of the conduit 104 and received by another of the sensing devices 102 or may be reflected and received by the transmitting sensing device 102. Accordingly, transmitted and/or reflected electromagnetic waves may be acquired at one of the ports. The term 'transmitted' and 'reflected' electromagnetic waves as used herein may be used to refer to transmitted/reflected electrical signals. Such electrical signals may be measured using at least one of a voltage value, a current value, and a power value. The electronic device of the EMFGR unit 108 may be configured to measure S-parameters corresponding to the transmitted or reflected electromagnetic waves received at the ports. The controller 110 may be configured to determine the amplitude and the phase angle corresponding to the transmitted or reflected electromagnetic waves based on the S-parameters.

Further, the controller 110 may be employed to determine the salinity in the multi-phase fluid based on the transmission or reflection coefficients of the transmitted or reflected electromagnetic waves. The determination of salinity in the multi-phase fluid is used to compensate measurements made for phase fraction determination in the fluid. The phase-fractions may be determined by measuring a complex permittivity of the fluid and utilizing a relationship between the complex permittivity and the phase fractions of phases in the fluid.

Figure 2:
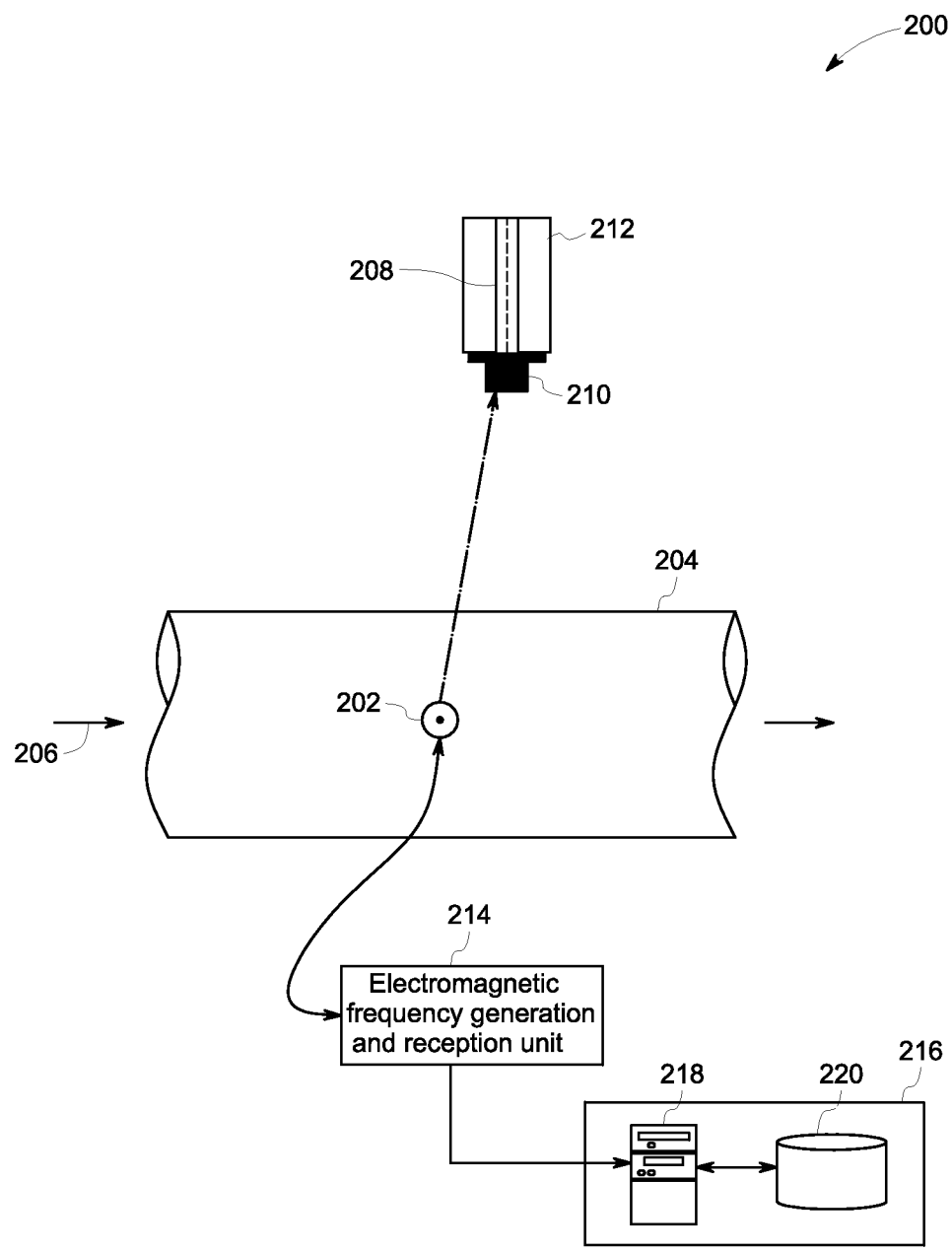
FIG. 2 is diagrammatical representation of a multi-phase flow measurement system configured to determine saline content in a multi-phase fluid, according to an embodiment of the present invention.

FIG. 2 is diagrammatical representation of a multi-phase flow measurement system configured to determine saline content in a multi-phase fluid, according to an embodiment of the present invention. The system 200 includes a sensing device 202 that is configured to emit electromagnetic waves of a range of frequencies in the multi-phase fluid 206 flowing through the conduit 204. The sensing device 202 includes among others an antenna 208, an RF connector 210 and a metallic holder 212.

In one embodiment, the antenna 208 is an open-ended coaxial probe that is configured to receive control signals from the RF connector 210 and emit electromagnetic waves into the multi-phase fluid. Some electromagnetic waves transmit through the multi-phase fluid 206 flowing through the conduit 204. However, some waves are reflected back from the multi-phase fluid 206. Fluid analysis is dependent on the transmitted or reflected electromagnetic waves. The antenna 208 is configured to receive these transmitted or reflected electromagnetic waves. The antenna 208, according to certain other embodiments, may be a patch antenna. In other embodiments, the antenna 208 may include a monopole antenna, a dipole antenna, or a multi-pole antenna.

The RF connector 210 of the sensing device 202 is coupled with the antenna 208. The RF connector 210, in turn, may be coupled to the EMFGR unit 214. The RF connector 210 is configured to be coupled to the EMFGR unit 214 to receive inputs from the controller 216 through the EMFGR unit 214. Signals from the controller 216 provide instructions on the amount of power to be supplied to the antenna 208.

The antenna 208 may be covered by the metallic holder 212 such that a substantial portion of the antenna 208 is covered leaving at least one surface open for direct contact with the multi-phase fluid 206 flowing through the conduit 204. In certain other embodiments, a surface of the sensing device 202 that is placed in the conduit 202 may also include one or more protective layers. The protective layers may be configured to protect the antenna 208 from coming in direct contact with the fluid 206 while allowing for electromagnetic waves to flow into the conduit 202. The protective layers may be made from non-conductive materials and also may include materials that are flexible in nature.

In operation, one or more sensing devices 202 are placed along the circumference of the conduit 204 to measure various parameters of the multi-phase fluid 206. The EMFGR unit 214 receives an input from the controller 216 to excite one or more sensing devices 202 with appropriate amount of power so that at least one of the antennas 208 coupled to the EMFGR unit 214 emits electromagnetic waves of a range of frequencies into the multi-phase fluid 206. Further, the sensing devices 202 are also configured to receive transmitted or reflected electromagnetic waves from the multi-phase fluid 206 in the conduit 204.

The transmitted or reflected electromagnetic waves that are received by the sensing devices 202 are communicated to the controller 216 through the EMFGR unit 214. The processing unit 218, which may be a part of the controller 216, is configured to determine a plurality of parameters from at least one of the transmitted and reflected electromagnetic waves. Examples of the plurality of parameters determined by the processing unit 218 include, but are not limited to, conductance (G), susceptance (B), differential conductance ($\Delta G$), differential susceptance ($\Delta B$), a real part of complex permittivity, and an imaginary part of complex permittivity.

According to one embodiment, the processing unit 218 is configured to determine an intermediate parameter related to the transmitted or reflected electromagnetic waves. Examples of intermediate parameter determined by the processing unit 218 include, but are not limited to, a complex reflection coefficient associated with the reflected electromagnetic waves, and a complex transmission coefficient associated with the transmitted electromagnetic waves. The intermediate parameter is utilized to obtain values of the plurality of parameters. According to one embodiment, when the intermediate parameter is the complex reflection coefficient, a value of admittance (Y) is determined using Equation 1:

$$Y_L^* = Y_0^* \left( \frac{1 - \Gamma^*}{1 + \Gamma^*} \right) \quad (1)$$

where YL* is the admittance associated with the antenna 208, Y0* is characteristic admittance, and Γ* is the complex reflection coefficient.

The admittance (YL*) associated with the antenna 208 may be expressed in terms of conductance (G) and susceptance (B) as shown in Equation 2:

$$Y_L^* = G + jB \quad (2)$$

The computed value of YL* is a complex number that is equated to the complex equation shown in Equation 2. The real part of the complex value of YL* is equated with the real part of Equation 2 and the imaginary part of the complex value of YL* is equated with the imaginary part of Equation 2. The values of G and B thus obtained are utilized to determine the estimated value of the real part ($\in'$) of complex permittivity and the estimated value of the imaginary part ($\in''$) of complex permittivity.

Further, complex admittance is also expressed in terms of real part of complex permittivity and imaginary part of complex permittivity using Equation 3:

$$Y_L^* = \omega C_f \in'' + G_{rad} \in'^{5/2} + \omega(C_0 + \in'(C_f)) \quad (3)$$

where, ω is the frequency of the transmitted or reflected electromagnetic waves, C0 and Cf are calibration constants associated with the sensing device 202, and Grad is value of conductance dependent on the frequency of the emitted electromagnetic waves.

Equations 2 and 3 are compared to establish a relationship between the real part ($\in'$) of complex permittivity and the imaginary part ($\in''$) of complex permittivity with conductance (G) and susceptance (B). This relationship is expressed in Equations 4 and 5.

$$G = \omega C_f \in'' + G_{rad} \in'^{5/2} \quad (4)$$

$$B = \omega(C_0 + \in'(C_f)) \quad (5)$$

Further, the processing unit 218 is configured to determine the salinity of the multi-phase fluid based on the values of estimated value of the real part ($\in'$) of complex permittivity and the estimated value of the imaginary part ($\in''$) of complex permittivity the multi-phase fluid. The processing unit 218, according to one embodiment, is configured to identify one or more records from a data repository, such as the data repository 220, corresponding to a first ratio between the estimated values of the imaginary part ($\in''$) of complex permittivity and the estimated values of the real part ($\in'$) of complex permittivity. Each record in the repository 220 corresponds to a particular value of salinity of the multi-phase fluid 206 for a particular value of the first ratio between the values of the imaginary part ($\in''$) of complex permittivity and the values of the real part ($\in'$) of complex permittivity.

According to one embodiment, the processing unit 218 may compute an average of salinity values from the one or more records and estimate the salinity of the multi-phase fluid 206. Further, the processing unit 218 may also be configured to select a maximum value of salinity among the one or more records as the salinity of the multi-phase fluid 206.

In another embodiment, the processing unit 218 may be configured to determine salinity of the multi-phase fluid 206 based on the estimated values of the real and imaginary parts of permittivity and computed values of real and imaginary parts of permittivity. In this embodiment, the processing unit 218 is configured to determine computed values of the real part of complex permittivity and computed values of the imaginary part of complex permittivity using a feed-forward model. The feed-forward model includes a relationship between the real and imaginary parts of complex permittivity, the one or more frequencies of the electromagnetic waves, temperature of the multi-phase fluid 206, and salinity of the multi-phase fluid. In one embodiment, the feed-forward model comprises Stogryn model that relates permittivity, salinity and temperature of water in the multi-phase fluid. The Stogryn model is described in "Equations for calculating the dielectric constant of saline water", IEEE Transactions on Microwave Theory and Techniques, August 1971, pp. 733-36. The processing unit 218 is configured to insert different values of salinity in the feed-forward model to determine computed values of the real and imaginary part of complex permittivity.

Further, the processing unit 218 is also configured to determine a second ratio between the computed value of the imaginary part of permittivity and the computed value of the real part of permittivity. The processing unit 218 is then configured to compare the second ratio and the first ratio between the estimated values of real part of complex permittivity and imaginary part of complex permittivity. Furthermore, the processing unit 218 selects that value of salinity from the different values of salinity inserted in the feed-forward model as the actual salinity value of the multi-phase fluid 206 for which the difference between the first ratio and the second ratio is less than or equal to a first threshold. In one embodiment, a minimum value of the difference between the first ratio and the second ratio is selected as the first threshold.

According to another embodiment, the processing unit 218 may be configured to compute the salinity values based on values of conductance (G) and susceptance (B) determined from Equations 1 and 2. The processing unit 218, according to one embodiment, is configured to determine a third ratio between the estimated value of conductance and the estimated value of susceptance. The processing unit 218 is further configured to determine one or more records from the data repository 220 corresponding to the third ratio. The one or more records may relate values of the third ratio with the salinity value for multi-phase fluid. The processing unit 218 is further configured to determine the salinity value of the multi-phase fluid based on the one or more records.

Further, the processing unit 218 may also or instead be configured to determine salinity of the multi-phase fluid 206 based on a fourth ratio between the estimated values of differential conductance and the estimated values of differential susceptance. The values for differential conductance (ΔG) and differential susceptance (ΔB) may be computed by computing values of G and B for different values of complex reflection coefficient or complex transmission coefficient. The values for G and B may be computed using Equations 1 and 2.

In one embodiment, the processing unit 218 may be configured to estimate salinity values based on one or more records stored in the data repository 220 that correlate the values of the fourth ratio with salinity values.

The data repository 220 may be populated with correlation data between the first ratio and salinity, third ratio and salinity, and fourth ratio and salinity utilizing test multiphase fluid samples with known salinity values. Values of G, B, ΔG, ΔB, ∈', and ∈" are estimated from the transmitted and reflected electromagnetic waves received from the test samples. The estimated values are then correlated with the known salinity values to populate the repository 220.

The processing unit 218, in certain embodiments, may comprise one or more central processing units (CPU) such as a microprocessor, or may comprise any suitable number of application specific integrated circuits working in cooperation to accomplish the functions of a CPU. The processing unit 218 may include a memory. The memory can be an electronic, a magnetic, an optical, an electromagnetic, or an infrared system, apparatus, or device. Common forms of memory include hard disks, magnetic tape, Random Access Memory (RAM), a Programmable Read Only Memory (PROM), and EEPROM, or an optical storage device such as a re-writeable CDROM or DVD, for example. The processing unit 218 is capable of executing program instructions, related to the determination of phase fractions in the multi-phase fluid, and functioning in response to those instructions or other activities that may occur in the course of or after determining phase fractions. Such program instructions will comprise a listing of executable instructions for implementing logical functions. The listing can be embodied in any computer-readable medium for use by or in connection with a computer-based system that can retrieve, process, and execute the instructions. Alternatively, some or all of the processing may be performed remotely by additional processing units 218. The controller 216, and more specifically the processing unit 218 in the controller 216, may perform operations implemented in the form of models such as those that are required to determine salinity, or those required to determine permittivity values as described herein.

To transmit electromagnetic waves into the multi-phase fluid and to gather reflected electromagnetic waves from the multi-phase fluid, the sensing device 202 may be placed proximate to the conduit 204 in various ways. Various configurations of the sensing device 202 placement along the conduit 204 depend on a material of the conduit 204 and may include using a strap-on device to strap a plurality of sensing device 202 along an outer surface of the conduit 204.

In another embodiment, the antenna in the sensing device 202 may be a patch antenna. The patch antenna may have a plurality of substrates. In certain examples, the substrates may be manufactured from flexible material such as silicone, plastic, woven natural fibers, and other suitable polymers, copolymers, and combinations thereof. The material for the substrates may be selected such that the sensing device 202 is flexible in nature while being able to sustain high pressure and temperature.

Further, when the antenna is a patch antenna the sensing device 202 may also include a protective dielectric layer over a surface of the antenna such that the dielectric layer acts as a barrier between the antenna and the multi-phase fluid 206. The dielectric layer may be placed on or over the antenna or the antenna may be printed on the dielectric layer or embedded into the dielectric layer such that the antenna may be covered by the dielectric layer. The dielectric layer, according to certain embodiments, may be made from material that leads to minimum attenuation of the electromagnetic waves emitted by the antenna. Further, the dielectric layer may be made from material that is flexible in nature to allow for the layer to conform to the inner diameter of the conduit 204 when the sensing device 202 is fitted on the conduit 204. In certain examples, the dielectric layer can be fabricated using hard materials to conform to the inner surface of the conduit. Examples of materials that can be used to make the dielectric layer include, but are not limited to, polyetheretherketone (PEEK), silicone, PTFE-coated fabric, epoxy resin, fiberglass etc.

In case of patch antennas, the sensing device may also include a feed element that is coupled to the RF connector 210 of the sensing device 202 on one end and is coupled with the antenna on another end. The RF connector 210 may be coupled to the EMFGR unit 214 to receive inputs from the controller 216 through the EMFGR unit 214. Signals from the controller 216 provide instructions on the amount of power to be supplied to the antenna.

Patch antennas may also be arranged in different configurations such as a helical arrangement. The patch antennas may be configured to substantially surround the circumference of the conduit. In various embodiments, the shape of the patch antennas from the sensing device 202 may vary. The shape of the sensing device 202 in FIG. 2 may be a function of the shape used for the patch antenna in the sensing device 202. The shape of the patch antenna may form virtually any polygonal shape or combinations thereof. For example, the patch antenna may be rectangular in shape. In another example, the patch antenna may have a circular shape, a square shape, as well as an elliptical shape.

Figure 3:
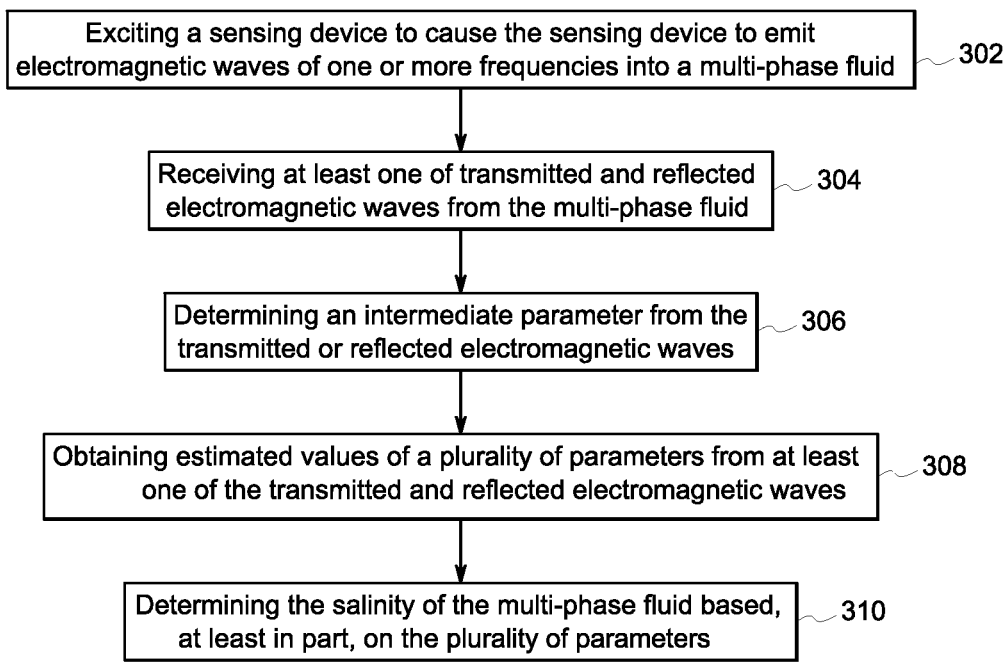
FIG. 3 is a flow chart representing a method for determination of saline content in multi-phase fluid, according to an embodiment of the present invention.

FIG. 3 illustrates a flow diagram of a method for determination of salinity in a multi-phase fluid. The illustrated method, according to one embodiment, can be utilized to determine salinity of the multi-phase fluid 206 flowing in the conduit 204 of FIG. 2. To determine salinity, a sensing device (for example: sensing device 202) is placed proximate to the multi-phase fluid 206. The sensing device, as described along with FIG. 2, includes an antenna 204.

The method includes, at step 302, exciting the sensing device to cause the sensing device to emit electromagnetic waves of one or more frequencies into the multi-phase fluid. In one embodiment, the one or more frequencies may be in the microwave frequency range. The electromagnetic waves may be emitted into the multi-phase fluid sequentially. At step 304 a plurality of transmitted or reflected electromagnetic waves are received by the sensing device from the multi-phase fluid. A part of the emitted electromagnetic waves travel through the multi-phase fluid to a side of the conduit that is opposite to the sensing device while some parts of the emitted waves are reflected back to the side of the conduit where the sensing device is placed. The electromagnetic waves that travel through the multi-phase fluid from the emission port (for example: ports 1) to the opposite side of the conduit (port 2) are termed as transmitted electromagnetic waves. On the other hand, the electromagnetic waves that get reflected after interaction with the multi-phase and collected back by the emission port (for example: port 1) are termed as reflected electromagnetic waves.

Further, at step 306, the transmitted or reflected electromagnetic waves are used to determine an intermediate parameter associated with the multi-phase fluid. Examples of intermediate parameter determined by the processing unit 218 include, but are not limited to, a complex reflection coefficient associated with the reflected electromagnetic waves, a complex transmission coefficient associated with the transmitted electromagnetic waves, amplitude of the reflected or transmitted electromagnetic waves, and phase angle of the reflected or transmitted electromagnetic waves. At step 308, the intermediate parameters are utilized to obtain an estimated value of a plurality of parameters of the multi-phase fluid 206. The estimated values of plurality of parameters include, but are not limited to, estimated value of conductance, estimated value of susceptance, estimated value of differential conductance, estimated value of differential susceptance, an estimated value of real part of complex permittivity and an estimated value of an imaginary part of complex permittivity. According to one embodiment, estimated values are determined utilizing the intermediate parameters determined from the transmitted or reflected electromagnetic waves. An example methodology to determine the estimated values involves utilizing Equations 1-5. At step 310, a salinity value associated with the multi-phase fluid is determined based on a relationship between at least one of the plurality of parameters and the salinity value.

In one embodiment, the relationship between the real and imaginary parts of permittivity and salinity may be expressed in terms of one or more records in a data repository. The records in the data repository, such as the data repository 220, may be populated by determining values of imaginary and real parts of permittivity for test fluid samples with known salinity values.

In another embodiment, the relationship between the real and imaginary parts of permittivity and salinity may be determined using a feed-forward model. The feed-forward model may be utilized to determine computed values of real and imaginary parts of permittivity by feeding one or more salinity values. The feed-forward model includes a relationship between permittivity, temperature, and salinity of water in the multi-phase fluid. The computed values are then compared with estimated values to determine the salinity of multi-phase fluid 206. The salinity value for which the difference between computed values and estimated values is less than or equal to a threshold may be identified as the salinity value for the multi-phase fluid 206.

According to other embodiments, the method also includes determining the estimated values of the real part of permittivity and imaginary part of permittivity from differential conductance and differential susceptance. The values for differential conductance ($\Delta G$) and differential susceptance ($\Delta B$) may be computed by computing values of G and B for different values of complex reflection coefficient or complex transmission coefficient. The values for G and B may be computed using Equations 1 and 2. According to some embodiments, salinity values can be determined using values of conductance and susceptance, or differential conductance and differential susceptance. The method may include determining one or more records that relate salinity values of test fluids with values of a ratio between conductance and susceptance for the test fluids. Further, the method may also include determining one or more records that relate salinity values of test fluids with values of a ratio between differential conductance and differential susceptance for the test fluids. The salinity value of the multi-phase fluid may be determined based on a comparison between the values of the ratios in the one or more records with the ratios of estimated values of conductance, susceptance, differential conductance, and differential susceptance.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of ordinary skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," etc. are used merely as labels, and are not intended to impose numerical or positional requirements on their objects.

This written description uses examples to disclose several embodiments of the invention, including the best mode, and also to enable any person of ordinary skill in the art to practice the embodiments of invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described method and system for determining salinity in multi-phase fluids, without departing from the spirit and scope of the invention herein involved, it is intended that all of the subject matter of the above description or shown in the accompanying drawings shall be interpreted merely as examples illustrating the inventive concept herein and shall not be construed as limiting the invention.

The invention claimed is:

1. A method of determining salinity of a multi-phase fluid in a conduit, comprising:
   exciting a sensing device to cause the sensing device to emit electromagnetic waves of one or more frequencies into a multi-phase fluid, wherein the sensing device is placed proximate to the multi-phase fluid;
   receiving electromagnetic waves corresponding to the electromagnetic waves of the one or more frequencies emitted by the sensing device into the multi-phase fluid;
   determining an intermediate parameter from the received electromagnetic waves, wherein the intermediate parameter is used to determine an admittance value;
   obtaining estimated values of at least one of a plurality of parameters based on the admittance value, wherein the estimated values of plurality of parameters comprise at least one of an estimated value of conductance, an estimated value of susceptance, an estimated value of differential conductance, an estimated value of differential susceptance, an estimated value of a real part of complex permittivity, and an estimated value of an imaginary part of complex permittivity;

computing a first ratio between the estimated value of the imaginary part of complex permittivity and the estimated value of the real part of complex permittivity;
computing a value of the real part of complex permittivity and a value of the imaginary part of complex permittivity;
determining a second ratio between the computed value of the imaginary part of complex permittivity and the computed value of the real part of complex permittivity;
computing a difference between the first ratio and the second ratio by comparing the first ratio to the second ratio; and
determining the salinity of the multi-phase fluid based, at least in part, on the difference between the first ratio and the second ratio, wherein
the sensing device includes an antenna and a radio frequency (RF) connector that is operatively coupled to the antenna;
the antenna is an open-ended coaxial probe configured to receive control signals from the RF connector and to emit the electromagnetic waves into the multi-phase fluid in accordance with the received control signals; and
a surface of the antenna is partially covered by a metallic holder such that the multi-phase fluid only directly contacts the antenna via a portion of the surface of the antenna uncovered by the metallic holder.

2. The method of claim 1, further comprising:
computing the values of the real and imaginary parts of complex permittivity using a feed-forward model by iteratively changing salinity values for the multi-phase fluid, wherein the feed-forward model comprises a relationship between the real and imaginary parts of the complex permittivity, the one or more frequencies, temperature of the multi-phase fluid, and the salinity of the multi-phase fluid; and
selecting a particular salinity value as the salinity of the multi-phase fluid when the difference between the first ratio and the second ratio is less than a first threshold.

3. The method of claim 1, further comprising:
identifying one or more records from a data repository corresponding to the first ratio, wherein each record corresponds to a particular value of salinity of the multi-phase fluid for a particular value of the first ratio; and
estimating the salinity of the multi-phase fluid based on the one or more records from the data repository.

4. The method of claim 1, further comprising:
identifying one or more records from a data repository corresponding to a ratio between the estimated values of conductance and susceptance, wherein each record corresponds to a particular value of salinity of the multi-phase fluid for a particular value of the ratio; and
estimating the salinity of the multi-phase fluid based on the one or more records from the data repository.

5. The method of claim 1, further comprising:
identifying one or more records from a data repository corresponding to a ratio between the estimated values of differential conductance and differential susceptance, wherein each record corresponds to a particular value of salinity of the multi-phase fluid for a particular value of the ratio; and
estimating the salinity of the multi-phase fluid based on the one or more records from the data repository.

6. The method of claim 1, wherein the intermediate parameter comprises at least one of a complex reflection coefficient and a complex transmission coefficient associated with the received electromagnetic waves.

7. The method of claim 1, wherein exciting the sensing device comprises exciting a coaxial probe.

8. A system for determining salinity of a multi-phase fluid flowing in a conduit, the system comprising:
a sensing device placed on or about the conduit and configured to emit electromagnetic waves of one or more frequencies; and
a controller configured to
excite the sensing device to emit electromagnetic waves of the one or more frequencies towards the multi-phase fluid,
receive electromagnetic waves corresponding to the electromagnetic waves of the one or more frequencies emitted by the sensing device into the multi-phase fluid,
determine an intermediate parameter from the received electromagnetic waves, wherein the intermediate parameter is used to determine an admittance value,
obtain estimated values of at least one of a plurality of parameters based on the admittance value, wherein estimated values of the plurality of parameters comprise at least one of an estimated value of conductance, an estimated value of susceptance, an estimated value of differential conductance, an estimated value of differential susceptance, an estimated value of a real part of complex permittivity, and an estimated value of an imaginary part of complex permittivity,
compute a first ratio between the estimated value of the imaginary part of complex permittivity and the estimated value of the real part of complex permittivity,
compute a value of the real part of complex permittivity and a value of the imaginary part of complex permittivity,
determine a second ratio between the computed value of the imaginary part of complex permittivity and the computed value of the real part of complex permittivity,
compute a difference between the first ratio and the second ratio by comparing the first ratio to the second ratio, and
determine the salinity of the multi-phase fluid based, at least in part, on the difference between the first ratio and the second ratio, wherein
the sensing device includes an antenna and a radio frequency (RF) connector that is operatively coupled to the antenna;
the antenna is an open-ended coaxial probe configured to receive control signals from the RF connector and to emit the electromagnetic waves into the multi-phase fluid in accordance with the received control signals; and
a surface of the antenna is partially covered by a metallic holder such that the multi-phase fluid only directly contacts the antenna via a portion of the surface of the antenna uncovered by the metallic holder.

9. The system of claim 8, wherein the antenna includes a patch antenna, a coaxial probe, a monopole antenna, a dipole antenna, an antenna feed, or a multi pole antenna.

10. The system of claim 8, wherein the intermediate parameter comprises at least one of a complex reflection coefficient and a complex transmission coefficient associated with the received electromagnetic waves.

11. The system of claim 8, wherein the controller is further configured to:

compute the values of the real and the imaginary part of complex permittivity using a feed-forward model by iteratively changing salinity values for the multi-phase fluid, wherein the feed-forward model comprises a relationship between the real and imaginary parts of complex permittivity, the one or more frequencies, temperature of the multi-phase fluid, and the salinity of the multi-phase fluid; and select a particular salinity value as the salinity of the multi-phase fluid when the difference between the first ratio and the second ratio is less than a first threshold.

12. The system of claim 8, wherein the controller is further configured to extract one or more records pertaining to a relationship between different values of salinity of the multiphase fluid and at least one of the first ratio between the estimated value of imaginary part of complex permittivity and the estimated value of real part of complex permittivity for the one or more frequencies;

a third ratio between the estimated value of conductance and the estimated value of susceptance; and a fourth ratio between the estimated value of differential conductance and the estimated value of differential susceptance.

13. The system of claim 12, further comprising a data repository configured to store the one or more records pertaining to the relationships between different values of salinity of the multi-phase fluid, the first ratio, the third ratio, and the fourth ratio.

* * * * *